March 21, 1972 S. HAKIM Re. 27,310

CEREBRO-VENTRICULAR CATHETER

Original Filed Jan. 3, 1968

INVENTOR.
SALOMON HAKIM

BY
Kenway, Jenney & Hildreth
ATTORNEYS

United States Patent Office

Re. 27,310
Reissued Mar. 21, 1972

27,310

CEREBRO-VENTRICULAR CATHETER

Salomon Hakim, 13 Carrera, 48–26 Bogota, Colombia

Original No. 3,516,410, dated June 23, 1970, Ser. No. 695,477, Jan. 3, 1968. Application for reissue Sept. 23, 1970, Ser. No. 74,544
Int. Cl. A61m *27/00*
U.S. Cl. 128—350 R 10 Claims

Matter enclosed in heavy brackets [ ] appears in the original patent but forms no part of this reissue specification; matter printed in italics indicates the additions made by reissue.

ABSTRACT OF THE DISCLOSURE

The invention is a ventricular catheter for use with ventriculo-atrial shunting devices, and consists of a tubing of soft, tissue-compatible material with intake apertures positioned in the wall of the tubing at one end thereof, the end of the tubing preferably being closed.

Thin membranes of flexible, tissue-compatible material are attached between the holes and extend outward from the wall of the tube. The flexibility is such that the lightest contact with attached tissue will bend the membrane and protect the underlying hole. The membrane may be radially slit to facilitate collapsing upon passing of the catheter through tissue. The membranes are long enough, so that when the catheter is inserted in tissue, they cover the apertures to prevent scraping of tissue thereby.

Background of invention

At the present time, there are several valve systems to provide ventriculo-atrial shunts to drain cerebrospinal fluid from the ventricles of the brain into the venous blood stream. Examples of these systems are U.S. Pat. 2,969,066 (Holter et al.); U.S. Pat. 3,020,913 (Heyer-Pudenz); and U.S. Pat. No. 3,288,142 (Hakim).

One of the main difficulties with prior art catheters is the plugging of the catheter drainage apertures by, for example, brain tissue debris which is produced by the scraping action of the apertures in the walls of the catheter at the time it is introduced into the ventricle. Also, changes in the ventricular cavity size may block off the drainage apertures because the walls of the ventricular cavity may obstruct the apertures, particularly when the catheter is short. Furthermore, contact of the catheter with the ventricular wall may obstruct one or more apertures.

Probably the worst enemy of proper drainage from the ventricular catheter is the choroid plexus. This organ normally floats free within the ventricular cavity and, thus, may accidentally come in contact with the drainage apertures of the catheter. When this happens, the constant stream of cerebrospinal fluid will elongate the plexus in the direction of the flow, causing it to enter the lumen of the catheter and eventually completely obstruct the flow therethrough.

Summary

Therefore, the purpose of the catheter of this invention is in general to avoid all the above difficulties by its construction, and, at the same time, to facilitate the proper positioning of the catheter within the ventricular cavity, since the construction of the catheter permits the surgeon to feel when the catheter has been correctly introduced and placed.

Therefore, among the several objects and provisions of the invention may be noted the provision of a catheter having means at one end for prevention of the blockage of the drainage apertures in said end of the catheter; the provision of a catheter of the above class in which said means is flexible and bendable so that it may be inserted through a small hole without damage to the human tissue which surrounds the hole; the provision of a catheter of either of the above classes in which the two functions are compatible, so that the means will assume its normal shape after having been passed through a hole and will act to prevent blockage of the apertures by any of several mechanisms; the provision of a catheter of the above types in which the means for preventing blockage of draining apertures is also effective to close off the latter during passage through tissue; the provision of a catheter of any of the above types in which both the catheter and the means for preventing blockage of the drainage apertures may be made integrally of the same material; and the provision of a catheter which is relatively simple to make and easy to sterilize and manipulate.

Other objects and advantages will be in part apparent and in part pointed out hereinafter.

The invention accordingly comprises the elements and combinations of elements, features of construction, and arrangements of parts which will be exemplified in the structure hereinafter described, and the scope of the application of which will be indicated in the appended claims.

In the accompanying drawings, in which one of various possible embodiments of the invention is illustrated:

Similar reference characters indicate corresponding parts throughout the several views of the drawings, and in the drawing dimensions of certain of the parts may have been modified and/or exaggerated for the purposes of clarity of illustration and understanding of the invention.

Figure 1:
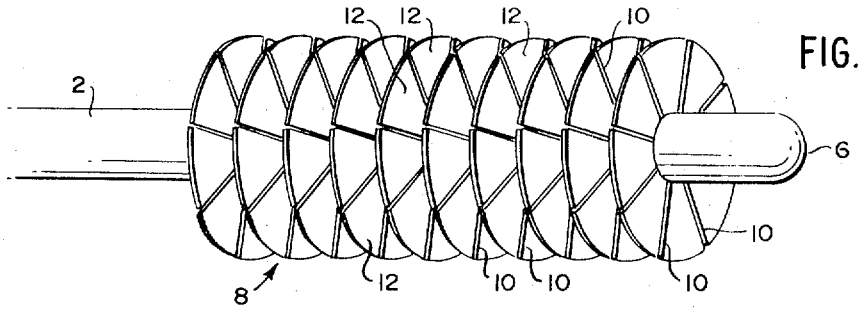
FIG. 1 is an enlarged illustration of an embodiment of the invention, showing the drainage end of a catheter, the remaining length of the catheter tubing being omitted since it is conventional.

Referring now to FIG. 1, there is shown a general view of the drainage end of a catheter of this invention, the catheter consisting of a tube 2 made of a soft tissue-compatible material such as silicone rubber. The tube 2 has a bore or lumen 4, and preferably has a closed end 6. If desired, the material of the catheter may contain, for example, five percent barium sulphate or other radiopaque material for the purpose of facilitating X-ray examination to show the position of the catheter within, for example, a ventricle into which it has been introduced. Attached to or forming part of the catheter at regular intervals are a plurality of radially extending membranes indicated generally by numeral 8, these membranes being also made of a soft flexible tissue-compatible material and may, preferably, be made of the same kind of silicone rubber as is made the tubing 2. The membranes are equally spaced along the end portion of the catheter, and preferably each membrane is slit as indicated by the slits 10 to form what might be called, for lack of a better name, the vanes 12. The purpose of slitting the membranes in this manner is to make each of the membranes more easily collapsible when the catheter is inserted through tissue, although the slits may be omitted if the membrane will collapse easily without them.

Figure 2:
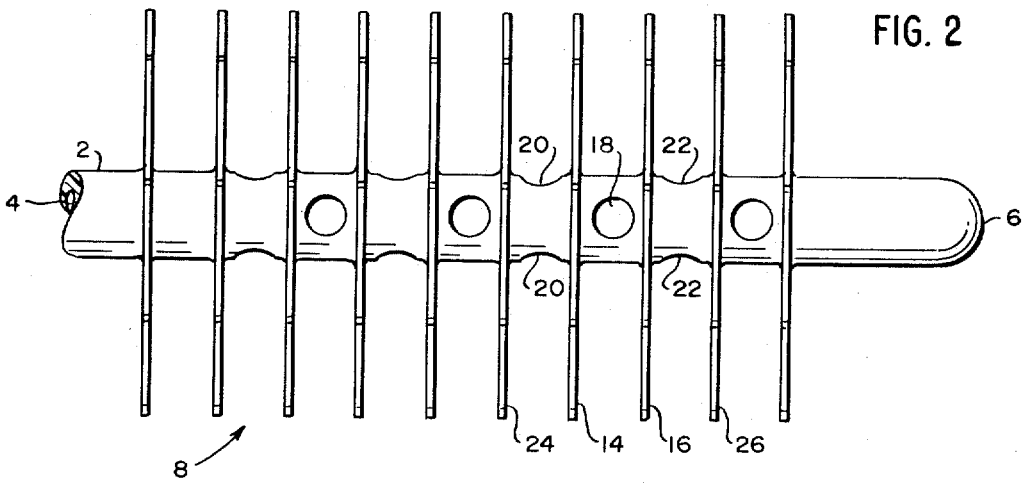
FIG. 2 is an elevation of the FIG. 1 embodiment the elevation again being enlarged for greater clarity.
Figure 3:
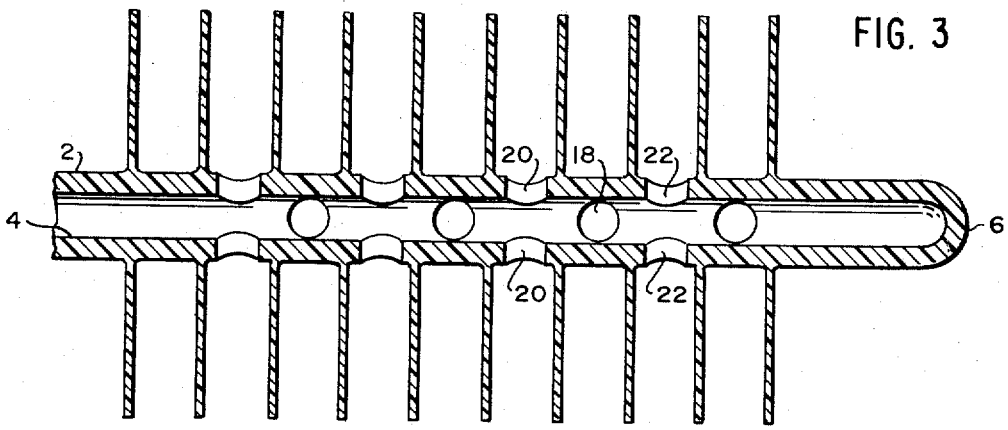
FIG. 3 is a cross-section of the FIG. 1 embodiment, given to show its manufacture in greater detail.

Between the membranes (for example, see FIG. 2, membranes 14 and 16) is provided in the wall of the tubing a pair of drainage apertures 18. Instead of a pair of drainage apertures 18, a single aperture may be used between adjacent membranes. However, for purposes of maximum drainage, it is preferred to have as many apertures as the structure will permit.

It will also be noticed that the diameters on which the pairs of apertures lie are angled successively to each other a matter of 90°. Of course, the 90° angle is arbitrary, and the angular relationship need not be used, or may be less than 90°, if desired.

Thus, while membranes 14 and 16 are on either side of apertures 18, membranes 14 and 24 are on either side of apertures 20, with membranes 16 and 26 on either side of aperture 22.

The membranes 8 may be molded, if desired, as an integral part of the tubing 2 when the tubing is molded. They may be separate discs as shown in the drawing, or they may consist of a continuous spiral of membranous material, the latter also being provided with slits 10. Or, the membranes 8 may first be blanked out of thin silicone and a hole slightly less in diameter than the outside diameter of tubing 2 may be formed at the center of the membranes. Then, each membrane is progressively slid over the end of the tubing 2 to its proper location, and attached thereto by a suitable cement compatible both with the silicone and with tissue. In manufacture, it is preferred to attach the membranes to the tubing 2, if they are to be attached separately, before making the apertures 18, 20, 22, etc. Or, during molding, with a suitably provided and designed mold, the membranes and the apertures can be molded at the end of the catheter during the time of molding.

Exemplary dimensions of the elements of this invention may be as follows: the outside diameter of the tubing 2 may be approximately 2.2 millimeters, the lumen 4 may be approximately 0.7 millimeter, each of the apertures 18, 20, 22, etc. may have a diameter of approximately 0.3 millimeter, the overall diameter of the membranes 8 may be approximately 8 millimeters, and the material of the membranes may be approximately 0.1 millimeter in thickness. Of course, depending upon the intended use of the catheter, these dimensions can be varied at will, but a requirement is always that the membranes be of such length and at such position to be able to cover the apertures when bent over or folded down.

As indicated in the summary, one of the advantages of the invention is that upon entering the tissue, the vanes 12 may collapse, and the radial extension of the membranes is such that when they are collapsed, they cover the apertures 18, 20, 22, etc. This feature automatically reduces the scraping effect on the brain tissue caused by the edges of the apertures during insertion, particularly through brain tissue and permits a large membrane structure to be inserted through a small hole. It also prevents simultaneous, accidental introduction of brain tissue into the apertures with resulting plugging thereof. However, as pointed out above, as soon as the membranes are free within the ventricular cavity, they return approximately to their normal position and open up the apertures, the membranes then acting as spacers, preventing stoppage of the apertures, and also preventing the drainage end of the tube proper and consequently its apertures from coming into direct contact with the ventricular walls. The membranes in their extended position act as a filter or block against the choroid plexus membranes, keeping them from coming in contact with the apertures in the catheter and thereby preventing the initial contact of the membrane with the holes.

The action of the membranes in performing the function of protecting the apertures is different from the use of fins or slots of a more or less rigid material. In the prior art, drainage apertures were placed at the bottom of a slot in the hope that if living tissue came in contact with the catheter, it would bridge the slot thus leaving the aperture free. However, if a filament of tissue were to lie nearly parallel to the slot, slight motion would cause it to align itself and drop into the slot, thus plugging the aperture. In the present invention, however, a thin strand of tissue lying against the membranes at even a slight angle will bend the membrane, thus causing it to tend to form a protective arch over the aperture while still allowing the entry of fluid from the side.

Another important feature of the flexible membrane is that they are self-cleaning due to the pulsation of the cerebrospinol fluid in the ventricles of the brain. It may be observed either by spinal tap or by observation of motion in and about the brain that pulsations due to the beating action of the heart are transmitted to the cerebrospinal fluid which surrounds the catheter. This pulsation causes a flexing of the membranes of the catheter with each heart beat. If the membranes were stiff instead of flexible, small particles of free brain material or blood could collect on the walls of the membranes and accumulate into a mass which would eventually occlude one or more of the apertures. However, the pulsating action of the flexible membranes tends to keep such particles off the walls so that a build-up of protein material is prevented. The flexible membrane structure is thus seen to be a dynamic, self-cleaning mechanism depending upon a wave motion affect produced by pulsation of the cerebrospinal fluid.

It will be noted in the drawings that holes are omitted between the proximal end membranes. This is an additional safety factor, since the end membrane can get no support in the direction away from the membrane array. Since it might thus more easily be bent away from its neighbor, apertures are omitted in this position.

Once the catheter is within the ventricular cavity, the operating surgeon can softly and gently pull the catheter backwardly to feel the resistance of the nearer membrane or disc against the ventricular wall. Slight reintroduction then assures the surgean of the exact position of the catheter in the ventricular cavity. If, for any reason, it should be desired to remove the catheter completely, it can be pulled out the same as it was introduced without harm to tissue, because of the ability of the vanes 12 to collapse.

In view of the above, it will be seen that the several objects of the invention are achieved and other advantageous results obtained.

It is to be understood that the invention is not limited in its application to the details of construction and arrangement of parts illustrated in the accompanying drawings, since the invention is capable of other embodiments and of being practiced or carried out in various ways. Also, it is to be understood that the phraseology or terminology employed herein is for the purpose of description and not of limitation.

As many changes could be made in the above constructions without departing from the scope of the invention, it is intended that all matter contained in the above description or shown in the accompanying drawings shall be interpreted as illustrative and not in a limiting sense, and it is also intended that the appended claims shall cover all such equivalent variations as come within the true spirit and scope of the invention.

Having described the invention, what is claimed is:

1. A ventricular catheter comprising a tube of soft, tissue-compatible material, a plurality of apertures in the wall of the tube spaced longitudinally along a portion of the length of the tube, and a plurality of membranes of flexible tissue-compatible material mounted along said portion and projecting radially outwardly of the tube, the membranes being generally parallel to each other and having their inner portions attached to the tube, each membrane being located along the tube between said apertures, said membranes being sufficiently closely spaced to prevent blockage of the apertures when they are normally extended within the ventrical and sufficiently resiliently flexible to collapse to cover the apertures as the catheter is inserted through brain tissue.

2. The catheter of claim 1 in which said portion is at the end portion of the catheter, and the end of the catheter is closed.

3. The catheter of claim 1 in which each membrane is slit radially from its central portion to its periphery to form vanes, thereby to increase the flexibility of the membrane structure as a whole, each vane in its normal position extending radially outward from the tube.

4. The catheter of claim 1 in which said membranes are discs, the membranes being located along said tube with one or more apertures being located between each pair of membranes.

5. The catheter of claim 4 in which the diameter on which any said pair of apertures is located is at an angle to the diameters on which adjacent pairs of apertures lie.

*6. A ventricular catheter comprising a tube of soft, tissue-compatible material, a plurality of apertures in the wall of the tube spaced longitudinally along a portion of the length of the tube, and a plurality of membranes of flexible tissue-compatible material mounted along said portion and projecting radially outwardly of the tube, each aperture being located along said tube adjacent to a membrane, said membranes being sufficiently closely spaced to prevent blockage of the apertures when they are normally extended within the ventrical and sufficiently resiliently flexible to collapse to cover the apertures as the catheter is inserted through brain tissue.*

*7. The catheter of claim 6 in which said portion is at the end portion of the catheter, and the end of the catheter is closed.*

*8. The catheter of claim 6 in which each membrane is slit radially from its central portions to its periphery to form vanes, thereby to increase the flexibility of the membrane structure as a whole, each vane in its normal position extending radially outward from the tube.*

*9. The catheter of claim 6 in which said membranes are discs, the membranes being located along said tube with one or more apertures being located between each pair of membranes.*

*10. The catheter of claim 9 in which the diameter on which any said pair of apertures is located is at an angle to the diameters on which adjacent pairs of apertures lie.*

References Cited

The following references, cited by the Examiner, are of record in the patented file of this patent or the original patent.

UNITED STATES PATENTS

| | | | |
|---|---|---|---|
| 724,913 | 4/1903 | Montgomery | 128—245 |
| 1,383,502 | 7/1921 | Vultee | 128—245 |
| 1,767,785 | 6/1930 | De Sushko | 128—341 X |
| 3,020,913 | 2/1962 | Heyer | 128—350 V |
| 3,428,046 | 2/1969 | Remer et al. | 128—349 R |
| 3,438,375 | 4/1969 | Ericson | 128—349 R |
| 3,136,316 | 6/1964 | Beall | 128—350 |

FOREIGN PATENTS

| | | | |
|---|---|---|---|
| 88,138 | 8/1896 | Germany | 128—350 |

DALTON L. TRULUCK, Primary Examiner

U.S. Cl. X.R.

128—245